(12) United States Patent
Das et al.

(10) Patent No.: US 8,722,389 B1
(45) Date of Patent: May 13, 2014

(54) METHOD AND SYSTEM OF CULTURING AN ALGAL MAT

(75) Inventors: Keshav C. Das, Athens, GA (US); Benjamin R. Cannon, Watkinsville, GA (US); Ashish Bhatnagar, Rajasthan (IN); Senthil Chinnasamy, Tamilnadu (IN)

(73) Assignee: U.S. Department of Energy, Washington, DC (US)

( * ) Notice: Subject to any disclaimer, the term of this patent is extended or adjusted under 35 U.S.C. 154(b) by 263 days.

(21) Appl. No.: 13/089,380

(22) Filed: Apr. 19, 2011

Related U.S. Application Data (60) Provisional application No. 61/325,396, filed on Apr. 19, 2010.

(51) Int. Cl.
*C12N 1/12* (2006.01)
*C12M 1/00* (2006.01)

(52) U.S. Cl.
USPC ........... 435/257.1; 435/257.3; 435/257.5; 435/288.5

(58) Field of Classification Search
None
See application file for complete search history.

(56) References Cited

U.S. PATENT DOCUMENTS

2010/0267122 A1* 10/2010 Chinnasamy et al. ..... 435/257.3
2013/0040380 A1* 2/2013 Hunt et al. ................ 435/292.1

* cited by examiner

*Primary Examiner* — Lisa J Hobbs
(74) *Attorney, Agent, or Firm* — John D Cravero; Brian J Lally; John T Lucas (57) ABSTRACT

A system and method for culturing algae are presented. The system and method utilize a fog of growth medium that is delivered to an algal mat generator along with a stream of $CO_2$ to promote growth of algal cells contained in the generator.

11 Claims, 4 Drawing Sheets

METHOD AND SYSTEM OF CULTURING AN ALGAL MAT

CROSS-REFERENCE TO RELATED APPLICATIONS

This application claims benefit and priority to U.S. Provisional Application No. 61/325,396, filed on Apr. 19, 2010, which is incorporated in its entirety by reference herein.

GOVERNMENT INTEREST

The United States Government has rights in this invention pursuant to Contract No. DE-FG36-05GO85012, between the U.S. Department of Energy (DOE) and University of Georgia Environmental Facility.

FIELD OF THE INVENTION

The present disclosure is generally related to systems and methods for culturing algae using a nebulized liquid growth medium delivery system and to methods for obtaining an algal biomass from such cultures for use in generating a biofuel.

BACKGROUND

The United States currently imports approximately two-thirds of its petroleum, 60% of which is used for producing transportation fuels. As global petroleum supplies diminish and in an effort to reduce the combustion of petroleum-based fuels believed by many to participate in climate change from greenhouse gas emissions, it has become increasingly important to find alternative, and preferably renewable, energy sources. The alternative energy sources explored to date include hydropower, solar power, wind power, nuclear power and bioenergy, among others.

Furthermore, in 2007, the Energy Independence and Security Act (EISA) was enacted, setting standards for vehicle fuel economy and including provisions promoting the use of renewable fuels. EISA establishes production requirements for domestic alternative fuels under the Renewable Fuel Standard that requires transportation fuel in the U.S. to contain a minimum of 36 billion gallons of renewable fuels, including advanced and cellulosic biofuels and biomass-based diesel, by 2022. While cellulosic ethanol is expected to play a major role in meeting these requirements, there are a number of next generation biofuels that can help reach that goal that are more sustainable than cellulosic ethanol.

One of the next generation biofuels with the potential to help the U.S. meet the RFS goals is biofuels derived from algae. As recognized in the Department of Energy's National Algal Biofuels Technology Roadmap (2010), which is incorporated by reference in its entirety herein, algal biofuels will play an important role in meeting these production requirements.

Algae are organisms that typically grow in aquatic environments using light and carbon dioxide ($CO_2$) to produce biomass, which can be used as potential biofuels, foods, feeds, high-value bioactives and can be used in bioremediation or as nitrogen fixing biofertilizers. Algae are classified as either macroalgae or microalgae, the latter being recognized as potentially good sources for biofuel production because of their relatively high oil content and their rapid biomass production. For example, potential oil yields from certain algae are projected to be 60 times higher than from soybeans and about 5 times more than oil palm per acre of land on an annual basis. In addition, microalgae grow very quickly (biomass can double as quickly as every 3.5 hours) compared to terrestrial crops and can be produced on non-arable land and using non-potable saline or waste water. Moreover, oil content in microalgae can exceed 80% by weight of dry mass, although levels of 20-50% are more common. Consequently, microalgae have recently garnered much attention from researchers, industry and the public as a source of biodiesel. However, microalgae can also be used to produce several other types of renewable biofuels, such as methane produced by anaerobic digestions of algal biomass and photobiologically produced biohydrogen.

Algal biomass consists of carbohydrate, proteins, and lipids or natural oils. Most of the natural oil produced by microalgae is in the form of triglycerol. The production of biodiesel from microalgae generally follows the production of biodiesel from plant and animal oils in that triglycerides are reacted with methanol, i.e., transesterification, to produce methyl esters of fatty acids (biodiesel) and glycerol. The transesterification is catalyzed by acids, alkalides and lipase enzymes.

Current algae cultivation methods include photobioreactors, raceways and open ponds. A raceway, or open pond, is a closed system about one foot deep in which algae are cultivated in conditions nearly identical to their natural environment. The pond is designed in a raceway configuration in which a paddlewheel provides circulation and mixing of algal cells and nutrients. The algal culture is fed in front of the paddlewheel during daylight while broth is harvest behind the wheel upon completion of a circulation loop. Because open ponds/raceways are open-air systems, they lose a substantial amount of water to evaporation and do not efficiently use $CO^2$. In addition, raceways often suffer contamination from undesirable algae and microorganisms and can suffer low biomass concentration due to dark zones below the surface and initial algae layer of the pond. Finally, optimal culture conditions can be difficult to maintain and recovery of the algal biomass is expensive.

Another current method of culturing algae is through the use of photobioreactors, which were pursued to overcome the contamination and evaporation problems associated with open ponds. A typical, tubular photobioreactor has a number of transparent tubes usually less than 10 cm oriented to maximize sunlight capture. Microalgal broth is circulated from a reservoir to the solar collectors (tubes) and back to the reservoir, with a portion of the algal being harvested after the solar collection tubes. Because a photobioreactor is a closed system, oxygen produced during photosynthesis builds up until it inhibits algae growth and, therefore, the algal culture must be returned to a degassing zone where the excess oxygen is removed. In addition, photobioreactors require temperature maintenance and are very difficult and expensive to scale up. Finally, photobioreactors may require periodic cleaning due to biofilm formation and often have dark zones below the outermost algal layer where light intensity is not sufficient to promote algal growth thereby leading to inefficiencies.

In order to overcome some of the noted deficiencies of photobioreactors and open ponds, Applicants have devised the system and methods described herein.

SUMMARY

One or more embodiments consistent with the present disclosure are directed to systems and methods that: (1) increase algae productivity for a given volume of space; (2) reduce water demand typical of algae growth; (3) efficiently deliver and use nutrients that promote algae growth; (4) allow use of a greater diversity of substrates for algae growth; and, (5) accommodate less energy intensive methods for harvesting of algae.

One or more embodiments consistent with the present disclosure relates to systems for culturing algae, the system comprising a liquid reservoir, a fog chamber, an algal mat generator chamber and a light source. Further aspects of systems consistent with the present disclosure include a liquid reservoir that has a first inlet and outlet for receiving and delivering a growth medium, respectively, to the fog chamber via a connecting tube. The fog chamber may have a first inlet for receiving the liquid growth medium and a second inlet for receiving $CO_2$ from a $CO_2$ source, and is further adapted to produce a stream of nebulized growth medium ("fog") that is subsequently delivered to the algal mat generator chamber with $CO_2$ via a first outlet. The algal mat generator chamber has a first inlet for receiving the stream of nebulized growth medium and $CO_2$ from the fog chamber. The system may further comprise a light source and preferably includes at least one solid support in the generator chamber on which to grow a population of algal cells. In yet another embodiment, the system may include means for harvesting the algae from the one or more solid supports.

Yet another aspect consistent with the present disclosure relates to methods of generating an algal culture comprising: (a) delivering a population of algal cells to a solid support contained in a closed environment; (b) exposing the population of algal cells to a nebulized growth medium; and, (c) maintaining the algal cells under conditions suitable for growth of the algae. Further embodiments include the steps of providing a source of $CO_2$ to the closed environment and exposing the algal cells to a light source. Still more aspects consistent with the disclosure include the steps of harvesting the algal cells from the solid support and collecting condensed growth medium from the closed environment and returning to the closed environment as a nebulized medium.

Still another aspect consistent with the present disclosure relates to methods of producing a biofuel comprising: (a) delivering a population of algal cells to a solid support contained in a closed environment; (b) exposing the population of algal cells to a nebulized growth medium; and, (c) maintaining a population algal cells under conditions suitable for growth of the algae, (d) isolating the algae from the solid support, and, (e) obtaining from the isolated algae a biofuel or a lipid material that is convertible to a biofuel. The conditions suitable for growth of the algae may include introducing light and $CO_2$ to the closed environment.

One aspect of the multiple embodiments is the ability to grow more algae in a given volume of space through the use of multiple surfaces that are spaced relatively closely to each other. For example, suspended liquid cultures typically have productivity of about 20 $g/m^2/d$ in a raceway having 20 cm depth. In contrast, one or more embodiments of the present invention can have more than 50 $g/m^2/d$ productivity on a single horizontal surface. However, in order to increase productivity, in one or more embodiments, one or more support surfaces may be placed vertically, thereby increasing productivity for every vertical surface placed in the generator chamber.

BRIEF DESCRIPTION OF THE DRAWINGS

These and other features, aspects, and advantages of the multiple embodiments of the present invention will become better understood with reference to the following description, appended claims, and accompanied drawings where:

The details of some exemplary embodiments of the methods and systems of the present disclosure are set forth in the description below. Other features, objects, and advantages of the disclosure will be apparent to one of skill in the art upon examination of the following description, drawings, examples and embodiments. It is intended that all such additional systems, methods, features, and advantages be included within this description, be within the scope of the present disclosure.

DETAILED DESCRIPTION

Prior to describing the various embodiments of the present invention, the following definitions are provided and should be used unless otherwise is indicated.

DEFINITIONS

In describing the disclosed subject matter, the following terminology will be used in accordance with the definitions set forth below.

The term "algae" as used herein refers to any organisms with chlorophyll and, in other than unicellular algae, a thallus not differentiated into roots, stems and leaves, and encompasses prokaryotic and eukaryotic organisms that are photoautotrophic or facultative heterotrophs. The term "algae" includes macroalgae (such as seaweed) and microalgae. For certain embodiments of the disclosure, algae that are not macroalgae are preferred. The terms "microalgae" and "phytoplankton," used interchangeably herein, refer to any microscopic algae, photoautotrophic or facultative heterotroph protozoa, photoautotrophic or facultative heterotroph prokaryotes, and cyanobacteria (commonly referred to as blue-green algae and formerly classified as Cyanophyceae). The use of the term "algal" also relates to microalgae and thus encompasses the meaning of "microalgal." The term "algal composition" refers to any composition that comprises algae, and is not limited to the body of water or the culture in which the algae are cultivated. An algal composition can be an algal culture, a concentrated algal culture, or a dewatered mass of algae, and can be in a liquid, semi-solid, or solid form. A non-liquid algal composition can be described in terms of moisture level or percentage weight of the solids. An "algal culture" is an algal composition that comprises live algae.

The algae of the disclosure can be a naturally occurring species, a genetically selected strain, a genetically manipulated strain, a transgenic strain, or a synthetic alga. Algae from tropical, subtropical, temperate, polar or other climatic regions can be used in the disclosure. Endemic or indigenous algal species are generally preferred over introduced species where an open culturing system is used. Algae, including microalgae, inhabit all types of aquatic environment, including but not limited to freshwater (less than about 0.5 parts per thousand (ppt) salts), brackish (about 0.5 to about 31 ppt salts), marine (about 31 to about 38 ppt salts), and briny (greater than about 38 ppt salts) environment. Any of such aquatic environments, freshwater species, marine species, and/or species that thrive in varying and/or intermediate salinities or nutrient levels, can be used in the embodiments of the disclosure. The algae in an algal composition of the disclosure may contain a mixture of prokaryotic and eukaryotic organisms, wherein some of the species may be unidentified. Fresh water from rivers, lakes; seawater from coastal areas, oceans; water in hot springs or thermal vents; and lake, marine, or estuarine sediments, can be used to source the algae. The algae may also be collected from local or remote bodies of water, including surface as well as subterranean water. Preferably, the algal species for use in the embodiments of the disclosure may be isolated from water or soil that has been in contact with high volumes of carpet industry wastewater for a prolonged period. This period of exposure will advantageously enrich the population of algae proliferating therein in those species and strains of algae able to utilize the wastewater as a nutrient source. It is not required that all the algae in an algal composition of the disclosure be taxonomically classified or characterized for the composition be used in the present disclosure. Algal compositions including algal cultures can be distinguished by the relative proportions of taxonomic groups that are present.

One or more species of algae are present in the algal composition of the disclosure. In one embodiment of the disclosure, the algal composition is a monoculture, wherein only one species of algae is grown. However, in many open culturing systems, it may be difficult to avoid the presence of other algae species in the medium. Accordingly, a monoculture may comprise about 0.1% to 2% cells of algae species other than the intended species, i.e., up to 98% to 99.9% of the algal cells in a monoculture are of one species. In certain embodiments, the algal compositions comprise an isolated species of algae, such as an axenic culture. In other embodiments, the algal composition can be a mixed culture that comprises more than one species of algae, i.e., the algal culture is not a monoculture. Such a culture can occur naturally with an assemblage of different species of algae or it can be prepared by mixing different algal cultures or axenic cultures. In certain embodiments, an algal composition comprising a combination of different batches of algal cultures is used in the disclosure. The algal composition can be prepared by mixing a plurality of different algal cultures. The different taxonomic groups of algae can be present in defined proportions. The combination and proportion of different algae in an algal composition can be designed or adjusted to yield a desired blend of algal lipids.

A mixed algal composition of the disclosure comprises one or several dominant species of macroalgae and/or microalgae. Microalgal species can be identified by microscopy and enumerated by counting, by microfluidics, or by flow cytometry, which are techniques well known in the art. A dominant species is one that ranks high in the number of algal cells, e.g., the top one to five species with the highest number of cells relative to other species. Microalgae occur in unicellular, filamentous, or colonial forms. The number of algal cells can be estimated by counting the number of colonies or filaments. Alternatively, the dominant species can be determined by ranking the number of cells, colonies and/or filaments. This scheme of counting may be preferred in mixed cultures where different forms are present and the number of cells in a colony or filament is difficult to discern. In a mixed algal composition, the one or several dominant algae species may constitute greater than about 10%, about 20%, about 30%, about 40%, about 50%, about 60%, about 70%, about 80%, about 90%, about 95%, about 97%, about 98% of the algae present in the culture. In certain mixed algal composition, several dominant algae species may each independently constitute greater than about 10%, about 20%, about 30%, about 40%, about 50%, about 60%, about 70%, about 80% or about 90% of the algae present in the culture. Many other minor species of algae may also be present in such compositions but they may constitute in aggregate less than about 50%, about 40%, about 30%, about 20%, about 10%, or about 5% of the algae present. In various embodiments, one, two, three, four, or five dominant species of algae are present in an algal composition. Accordingly, a mixed algal culture or an algal composition can be described and distinguished from other cultures or compositions by the dominant species of algae present. An algal composition can be further described by the percentages of cells that are of dominant species relative to minor species, or the percentages of each of the dominant species. It is to be understood that mixed algal cultures or compositions having the same genus or species of algae may be different by virtue of the relative abundance of the various genus and/or species that are present. It is understood that for the purposes of the embodiments of the disclosure, the populations of algae, either monoculture or mixed populations are characterized as being able to proliferate on a medium comprising carpet industry wastewater, either untreated or treated to further comprise an amount of city sewage that allows growth of the algae to preferably increase over the growth rate in the absence of the added sewage. It is further understood that with a mixed population of algae, two or more of the species or strains of the mixed population may differ in their growth rates when cultured on carpet industry wastewater-based media.

It should also be understood that in certain embodiments, such algae may be present as a contaminant, a non-dominant group or a minor species, especially in an open system. Such algae may be present in negligent numbers, or substantially diluted given the volume of the culture or composition. The presence of such algal genus or species in a culture, composition or a body of water is distinguishable from cultures, composition or bodies of water where such algal genus or species are dominant, or constitute the bulk of the algae. In various embodiments, one or more species of algae belonging to the following phyla can be used in the systems and methods of the disclosure: Cyanobacteria, Cyanophyta, Prochlorophyta, Rhodophyta, Glaucophyta, Chlorophyta, Dinophyta, Cryptophyta, Chrysophyta, Prymnesiophyta (Haptophyta), Bacillariophyta, Xanthophyta, Eustigmatophyta, Rhaphidophyta, and Phaeophyta. In certain embodiments, algae in multicellular or filamentous forms, such as seaweeds and/or macroalgae, many of which belong to the phyla Phaeophyta or Rhodophyta, are less preferred. In certain embodiments, the algal composition of the disclosure comprises cyanobacteria (also known as blue-green algae) from one or more of the following taxonomic groups: Chroococcales, Nostocales, Oscillatoriales, Pseudanabaenales, Synechococcales, and Synechococcophycideae. Non-limiting examples include *Gleocapsa, Pseudoanabaena, Oscillatoria, Microcystis, Synechococcus* and *Arthrospira* species.

In certain embodiments, the algal composition of the disclosure comprises algae from one or more of the following taxonomic classes: Euglenophyceae, Dinophyceae, and Ebriophyceae. Non-limiting examples include *Euglena* species and the freshwater or marine dinoflagellates.

In certain embodiments, the algal composition of the disclosure comprises green algae from one or more of the following taxonomic classes: Micromonadophyceae, Charophyceae, Ulvophyceae and Chlorophyceae. Non-limiting examples include species of *Borodinella, Chlorella* (e.g., *C. ellipsoidea*), *Chlamydomonas, Dunaliella* (e.g., *D. salina, D.*

*bardawil*), *Franceia, Haematococcus, Oocystis* (e.g., *O. parva, O. pustilla*), *Scenedesmus, Stichococcus, Ankistrodesmus* (e.g., *A. falcatus*), *Chlorococcum, Monoraphidium, Nannochloris* and *Botryococcus* (e.g., *B. braunii*).

In certain embodiments, the algal composition of the disclosure comprises golden-brown algae from one or more of the following taxonomic classes: Chrysophyceae and Synurophyceae. Non-limiting examples include *Boekelovia* species (e.g. *B. hooglandii*) and *Ochromonas* species.

In certain embodiments, the algal composition in the disclosure comprises freshwater, brackish, or marine diatoms from one or more of the following taxonomic classes: Bacillariophyceae, Coscinodiscophyceae, and Fragilariophyceae. Preferably, the diatoms are photoautotrophic or auxotrophic. Non-limiting examples include *Achnanthes* (e.g., *A. orientalis*), *Amphora* (e.g., *A. coffeiformis* strains, *A. delicatissima*), *Amphiprora* (e.g., *A. hyaline*), *Amphipleura, Chaetoceros* (e.g., *C. muelleri, C. gracilis*), *Caloneis, Camphylodiscus, Cyclotella* (e.g., *C. cryptica, C. meneghiniana*), *Cricosphaera, Cymbella, Diploneis, Entomoneis, Fragilaria, Hantschia, Gyrosigma, Melosira, Navicula* (e.g., *N. acceptata, N. biskanterae, N. pseudotenelloides, N. saprophila*), *Nitzschia* (e.g., *N. dissipata, N. communis, N. inconspicua, N. pusilla* strains, *N. microcephala, N. intermedia, N. hantzschiana, N. alexandrina, N. quadrangula*), *Phaeodactylum* (e.g., *P. tricornutum*), *Pleurosigma, Pleurochrysis* (e.g., *P. carterae, P. dentata*), *Selenastrum, Surirella* and *Thalassiosira* (e.g., *T. weissflogii*).

In certain embodiments, the algal composition of the disclosure comprises one or more algae from the following groups: *Coelastrum, Chlorosarcina, Micractinium, Porphyridium, Nostoc, Closterium, Elakatothrix, Cyanosarcina, Trachelamonas, Kirchneriella, Carteria, Crytomonas, Chlamydamonas, Planktothrix, Anabaena, Hymenomonas, Isochrysis, Pavlova, Monodus, Monallanthus, Platymonas, Pyramimonas, Stephanodiscus, Chroococcus, Staurastrum, Netrium*, and *Tetraselmis*.

In certain embodiments, any of the above-mentioned genus and species of algae may each be less preferred independently as a dominant species in, or be excluded from, an algal composition of the disclosure.

The term "photoautotroph" as used herein refers to organisms (usually plants) that carry out photosynthesis to acquire energy. Energy from sunlight is used to convert carbon dioxide and water into organic materials to be used in cellular functions such as biosynthesis and respiration. In an ecological context, they provide nutrition for all other forms of life (besides other autotrophs such as chemotrophs). In terrestrial environments, plants are the predominant variety, while aquatic environments include a range of phototrophic organisms such as algae (e.g. kelp), other protists (such as *euglena*) and bacteria (such as cyanobacteria). One product of this process is starch, which is a storage or reserve form of carbon, which can be used when light conditions are too poor to satisfy the immediate needs of the organism. Photosynthetic bacteria have a substance called bacteriochlorophyll, live in lakes and pools, and use the hydrogen from hydrogen sulfide instead of from water, for the chemical process. Cyanobacteria live in fresh water, seas, soil and lichen, and use a plant-like photosynthesis. The depth to which sunlight or artificial light can penetrate into water, so that photosynthesis may occur, is known as the phototrophic zone.

The term "autotroph" as used herein refers to an organism that produces complex organic compounds (carbohydrates, fats, and proteins) from simple inorganic molecules using energy from light (by photosynthesis) or inorganic chemical reactions. They are able to make their own food and can convert carbon dioxide into useful, solid compounds (such as long chain carbon compounds necessary for growth). Therefore, they do not utilize organic compounds as an energy source or a carbon source. Through reduction (a form of chemical reaction where hydrogen is added to the chemical chain), autotrophs can reduce carbon dioxide to organic compounds. The reduction of carbon dioxide, a low-energy compound, creates a store of chemical energy. Most autotrophs use water as the reducing agent, but some can use other hydrogen compounds such as hydrogen sulfide. Autotrophs are the producers in a food chain, such as plants on land or algae in water. Bacteria which derive energy from oxidizing inorganic compounds (such as hydrogen sulfide, elemental sulfur, ammonium and ferrous iron) are chemoautotrophs, and include the lithotrophs.

The term "heterotroph" as used herein refers to an organism that uses organic carbon for growth. This contrasts with autotrophs, such as plants, which can directly use sources of energy such as light to produce organic substrates from inorganic carbon dioxide.

The term "biomass" as utilized herein refers to the mass or accumulating mass of photosynthetic organisms resulting from the cultivation of such organisms using a variety of techniques.

The terms "photobioreactor," "photobioreactor apparatus", or "reactor" as used herein refer to an apparatus containing, or configured to contain, a liquid medium comprising at least one species of photosynthetic organism and having either a source of light capable of driving photosynthesis associated therewith, or having at least one surface at least a portion of which is partially transparent to light of a wavelength capable of driving photosynthesis (i.e. light of a wavelength between about 400-700 nm). Certain photobioreactors for use herein comprise an enclosed bioreactor system such as, but not limited to, a polybag, as contrasted with an open bioreactor, such as a pond or other open body of water, open tanks, open channels such as a raceway, and the like.

The term "raceway" as used herein refers to elongated (long and narrow) tanks or liquid paths that provide a flow-through system for a culture medium, thereby enabling a higher yield of biomass than would be achieved by a static pond system.

The term "biofuel" as used herein refers to fuel derived from biomass. The term "biomass" encompasses solid biomass, liquid fuels and various biogases. Bioethanol is an alcohol made by fermenting the sugar components of plant materials and it is made mostly from sugar and starch crops. With advanced technology being developed, cellulosic biomass, such as trees and grasses, are also used as feedstocks for ethanol production. Ethanol can be used as a fuel for vehicles in its pure form, but it is usually used as a gasoline additive. The predominant biogas produced from a biomass is typically methane but may also include minor percentages of other alkyl-chain gases and volatile compounds.

The term "biodiesel" as used herein refers to a vegetable oil- or animal fat-based diesel fuel consisting of long-chain alkyl (methyl, propyl or ethyl) esters. Biodiesel is typically made by chemically reacting lipids, such as derived from algae cultured by the methods of the present disclosure, with an alcohol. Biodiesel is produced from oils or fats using transesterification. Biodiesel is meant to be used in standard diesel engines and is distinct from the vegetable and waste oils. Biodiesel can be used alone, or blended with petrodiesel. The term "biodiesel" can be standardized as mono-alkyl ester in the United States.

Generally, a process for production of biofuels from algae can include cultivating oil-producing algae by promoting both autotrophic and heterotrophic growth. Heterotrophic growth can include introducing an algal feed to the oil-producing algae to increase the formation of algal oil. The algal oil can be extracted from the oil-producing algae using biological agents and/or other methods such as mechanical pressing. The resulting algal oil can be subjected to a transesterification process to form biodiesel.

The terms "transesterify," "transesterifying," and "transesterification" refer to a process of exchanging an alkoxy group of an ester by another alcohol and more specifically, of converting algal oil, e.g. triglycerides, to biodiesel, e.g. fatty acid alkyl esters, and glycerol. Transesterification can be accomplished by using traditional chemical processes such as acid or base catalyzed reactions, or by using enzyme-catalyzed reactions.

The term "nebulize" as used herein refers to the generation of a fine mist or fog of a liquid and is typically used in reference to a liquid growth medium. A "nebulized" liquid may also be described as a "fog", "mist", "vaporized liquid", "humidified liquid" or "atomized liquid" liquid. A "nebulized" liquid can be accomplished using a number of methods, including using a nebulizer, an atomizer, a jet nebulizer, an ultrasonic wave nebulizer, humidifier, vaporizer and many other methods know to one of skill in the art. Droplet sizes of a "nebulized" liquid medium may range from about 1 micron to about a few hundred microns.

An "algal mat" as used herein is a layer of algae that is created on a solid support contained within an algal mat generator.

"Fog chamber" as used herein is an enclosed environment in which a liquid growth medium is nebulized. As such, the fog chamber itself may be a nebulizer or may be associated with a nebulizer or other fog generating means.

Discussion

Algae have the potential to produce about 40,700-53,200 liters per hectare per annum of oil (Weyer et al., (2009) Bioenerg. Res. DOI 10.1007/s12155-009-9046-x), which is 6 to 8 times better than the yield of oil palm considered currently the best source for the purpose. Oil from algae can be used for biodiesel while residual biomass can be fermented into ethanol and biomethane.

Biofuels derived from plants like algae are considered "carbon neutral". Two of the most limiting factors to a sustainable and economic production of algae for biofuel purposes are water and fertilizers. Maximum cultivation of algae would require 2 million liters of water per hectare if grown in open ponds, but to compensate for evaporative losses a further 11 million liters would be required. Hence, water management is a critical bottleneck in practical algae cultivation.

Cultivation of algae can also require supplementation of nutrients, particularly nitrogen and phosphorus. Increasing fertilizer costs make economically feasible production of algae a still difficult target. It has been shown that wastewater generated by the carpet industry, when combined with a typical city sewage, can provide a cheap source of an algal culture medium while simultaneously being treated to reduce or remove the industry by-products that are undesired in the environment.

The production of energy in the form of oil (lipids) by algae is more useful than the production of starch. If equal volumes of oil and starch are produced, the oil will contain significantly more energy. For example, the energy content in a typical algal lipid is 9 kcal/gram compared to 4.2 kcal/gram for typical algal starch. In the production of sugars from starch, not all the starch is saccharified into sugars which can be easily fermented, so a portion may be lost as unused sugars. Also, the production of biodiesel from the algal oil is essentially energy-neutral, so nearly all of the energy content of the algal oil is retained in the biodiesel. In contrast, the production of alcohol from biomass or starch is less efficient, especially during the fermentation stage which converts the sugars derived from the biomass or starch into alcohol. Fermentation is exothermic, with heat being generated that must be removed and often wasted. One half of the carbon in the sugar is released during fermentation as carbon dioxide and is therefore not available for fuel energy. For all of these reasons biodiesel production is more efficient overall than bioethanol production, and therefore the goal of highest efficiency and lowest cost is served by maximizing biodiesel production.

Nevertheless, starch-producing or biomass-producing algae are an important aspect of the present disclosure. For example, starch products or sugars converted from algal biomass can be used to produce feed for the oil-producing algae and/or production of ethanol or ethyl acetate for use in transesterification of algal oil. Carbon dioxide released during fermentation can be fed back into the algal growth stage, substantially eliminating at least this form of energy loss in the fermentation process.

Harvesting of the algae from the solid supports can be accomplished in a number of ways, including simple mechanical scraping. For example, in an exemplary embodiment of vertical solid supports, the supports may be dried outside the growth chamber and, after a time, the algae would flake off naturally or could be brushed off with a mechanical brush, which would provide a dry algae powder. In an additional embodiment, the solid supports could be placed on a belt press where the supports are run over a roller and the algae scraped off as it passes on the roller. This form of harvesting may be done with moist or dry algae.

Mechanical crushing, for example, an expeller or press, a hexane or butane solvent recovery step, supercritical fluid extraction, or the like can also be useful in extracting the oil from oil vesicles of the oil-producing algae grown using the methods of the disclosure. Alternatively, mechanical approaches can be used in combination with biological agents in order to improve reaction rates and/or separation of materials.

Once the oil has been released from the algae it can be recovered or separated from a slurry of algae debris material, e.g. cellular residue, oil, enzyme, by-products, etc. This can be done by sedimentation or centrifugation, with centrifugation generally being faster. Starch production can follow similar separation processes. Recovered algal oil can be collected and directed to a conversion process. The algal biomass left after the oil is separated may be fed into the depolymerization stage described below to recover any residual energy by conversion to sugars, and the remaining husks can be either burned for process heat or sold as an animal food supplement or fish food.

Algal oil can be converted to biodiesel through a process of direct hydrogenation or transesterification of the algal oil. Algal oil is in a similar form as most vegetable oils, which are in the form of triglycerides. This form of oil can be burned directly. However, the properties of the oil in this form are not ideal for use in a diesel engine, and without modification, the engine will soon run poorly or fail. In accordance with the present disclosure, the triglyceride is converted into biodiesel, which is similar to but superior to petroleum diesel fuel in many respects.

One process for converting the triglyceride to biodiesel is transesterification, and includes reacting the triglyceride with alcohol or other acyl acceptor to produce free fatty acid esters and glycerol. The free fatty acids are in the form of fatty acid alkyl esters. Transesterification can be done in several ways, including biologically and/or chemically. The biological process uses an enzyme known as a lipase to catalyze the transesterification, while the chemical process may use, but is not limited to, a synthetic catalyst that may be either an acid or a base. With the chemical process, additional steps are needed to separate the catalyst and clean the fatty acids. In addition, if ethanol is used as the acyl acceptor, it must be essentially dry to prevent production of soap via saponification in the process, and the glycerol must be purified. Either or both of the biological and chemically-catalyzed approaches can be useful in connection with the processes of the present disclosure.

Algal triglyceride can also be converted to biodiesel by direct hydrogenation. In this process, the products are alkane chains, propane, and water. The glycerol backbone is hydrogenated to propane, so there is substantially no glycerol produced as a byproduct. Furthermore, no alcohol or transesterification catalysts are needed. All of the biomass can be used as feed for the oil-producing algae with none needed for fermentation to produce alcohol for transesterification. The resulting alkanes are pure hydrocarbons, with no oxygen, so the biodiesel produced in this way has a slightly higher energy content than the alkyl esters, degrades more slowly, does not attract water, and has other desirable chemical properties.

In the embodiments of this aspect of the disclosure, the population of algal cells can comprise at least one of the group consisting of: a marine algal strain, a freshwater (non-marine) algal strain, a cyanobacter strain, a diatomaceous algal strain, a plurality of marine algal strains, a plurality of freshwater (non-marine) algal strains, a plurality of cyanobacter strains, and a plurality of diatomaceous algal strains, or any combination thereof.

In the embodiments of this aspect of the disclosure, at least one algal strain of the population of algal cells can be isolated from a source in contact with a wastewater effluent from an industrial application, such as carpet industry wastewater.

In the embodiments of this aspect of the disclosure the population of algal cells can comprise an algal strain of a genus selected from the group consisting of: *Gloeocystis*, *Limnothrix*, *Scenedesmus*, *Chlorococcum*, *Chlorella*, *Anabaena*, *Chlamydomonas*, *Botryococcus*, *Cricosphaera*, *Spirulina*, *Nannochloris*, *Dunaliella*, *Phaeodactylum*, *Pleurochrysis*, *Tetraselmis*, and a combination thereof.

In the embodiments of this aspect of the disclosure, at least one algal strain of the population of algal cells can be selected from the group consisting of: a *Chlamydomonas* sp., *Chlorella vulgaris*, a *Chlorococcaceae* sp., *Chlorococcum humicola*, *Coelastrum microporum*, *Gloeocystis vesiculosa*, *Monoraphidium mirabile*, an *Oedogonium* sp., *Oocystis lacustris*, *Scenedesmus abundans*, *Scenedesmus acuminatus*, *Scenedesmus acutus*, *Scenedesmus acutus alternans*, *Scenedesmus bicaudatus*, *Scenedesmus bijuga*, *Scenedesmus bijuga alternans*, *Scenedesmus denticulatus*, *Scenedesmus dimorphus*, *Scenedesmus incrassatulus*, *Scenedesmus obliquus*, *Scenedesmus quadricauda*, *Scenedesmus quadrispina*, *Scenedesmus serratus*, a *Stigeoclonium* sp., *Ulothrix variabilis*, a *Uroglena* sp., an *Anabaena* sp, *Aphanocapsa delicatissima*, *Aphanocapsa hyalina*, an *Aphanothece* sp., *Calothrix braunii*, a *Chroococcaceae* sp., *Chroococcus minutus*, a *Cylindrospermopsis* sp., *Leibleinia kryloviana*, a *Limnothrix* sp., *Limnothrix redekei*, a *Lyngbya* sp., a *Nostoc* sp., an *Oscillatoria* sp., *Oscillatoria tenuis*, *Planktolyngbya limnetica*, *Raphidiopsis curvata*, *Synechococcus elongatus*, a *Synechococcus* sp., a *Synechocystis* sp., an *Eunotia* sp., *Navicula pelliculosa*, a *Navicula* sp., *Nitzschia palea*, *Nitzschia amphibia*, *Nitzschia pura*, *Gomphonema parvulum*, *Gomphonema gracile*, and a *Rhodomonas* sp.

In some embodiments of this aspect of the disclosure, the population of algal cells comprises at least one species selected from the group consisting of: *Botryococcus braunii* UTEX 572, *Chlorella protothecoides* UTEX 25, *Chlorella saccharophila* var. *saccharophila* UTEX 2469, *Chlorella vulgaris* UTEX 2714, *Cricosphaera carterae* UTEX LB1014, *Dunaliella tertiolecta* UTEX LB999, *Nannochloris oculata* UTEX LB1998, *Spirulina platensis* UTEX LB 1926, *Spirulina maxima* UTEX LB2342, *Tetraselmis suecica* UTEX LB2286, *Tetraselmis chuii* UTEX LB232, *Phaeodactylum tricornutum* UTEX 646, *Pleurochrysis carterae* CCMP 647, and a combination thereof.

In some embodiments, the population of algal cells can comprise a plurality of strains selected from the Group consisting of: *Botryococcus braunii* UTEX 572, *Chlorella protothecoides* UTEX 25, *Chlorella saccharophila* var. *saccharophila* UTEX 2469, *Chlorella vulgaris* UTEX 2714, *Cricosphaera carterae* UTEX LB1014, *Dunaliella tertiolecta* UTEX LB999, *Nannochloris oculata* UTEX LB1998, *Spirulina platensis* UTEX LB1926, *Spirulina maxima* UTEX LB2342, *Tetraselmis suecica* UTEX LB2286, *Tetraselmis chuii* UTEX LB232, *Phaeodactylum tricornutum* UTEX 646, and *Pleurochrysis carterae* CCMP 647.

In an embodiment of this aspect of the disclosure, the population of algal cells can be a consortium, where the consortium comprises *Gleocytis vesiculosa* strain 1, *Limnothrix redekei*, *Gleocytis vesiculosa* strain 2, *Scenedesmus* spp., *Limnothrix redekei*, *Chlorococcum humicola* strain 1, *Chlorococcum humicola* strain 2, *Chlorococcum humicola* strain 3, *Clorella vulgaris* strain 1, *Clorella vulgaris* strain 2, *Clorella vulgaris* strain 3, *Gleocytis vesiculosa* strain 3, *Anabaena* spp., *Gleocytis vesiculosa* strain 4, *Chlamydomonas* spp. In an embodiment of this aspect of the disclosure, the population of algal cells can be a consortium comprising *Chlamydomonas globosa*, *Chlorella minutissima*, and *Scenedesmus bijuga*.

In the embodiments of this aspect of the disclosure, the algal culture can be optionally provided with air supplemented with carbon dioxide.

In the embodiments of this aspect of the disclosure, the method can further comprise isolating the algal biomass from the medium.

Still another aspect of the present disclosure encompasses the method of generating an algal culture described above and further encompasses methods of producing a biofuel therefrom. The biofuel is generated after the algal mat is created through the further steps of: (a) isolating the algae from the solid support, and (b) obtaining from the algae a biofuel or a source of biofuel, such as a lipid that is convertible to a biofuel.

Yet another aspect of the disclosure encompasses a system for generating an algae culture, the system comprising: a liquid reservoir, a fog chamber, an algal mat generator, and a light source. The system may further include a CO2 source and may include a plurality of solid support surfaces in the algal mat generator. Yet another aspect of the system comprises a means for collecting the algae from solid supports. In yet another aspect, the system comprises a means for returning condensed growth medium from the algal mat generator to the fog chamber for recirculation, such as a flexible tube or inflexible vent or duct.

System for Generating an Algae Culture

A system for culturing algae comprising: (a) a liquid reservoir; (b) a fog chamber; (c) an algal mat generator chamber; and, (d) a light source, wherein the fog chamber is operably connected to the liquid reservoir to receive liquid from the liquid reservoir and adapted to receive $CO_2$ from a $CO_2$ source, further wherein the fog chamber is operably connected to the algal mat generator chamber in order to deliver a stream of $CO_2$ and a nebulized liquid medium to the algal mat generator chamber, and wherein the algal mat generator chamber is adapted to receive light from the light source.

In yet another embodiment, the system for culturing algae comprises: (a) a liquid reservoir having at least a first inlet and a first outlet, wherein the liquid reservoir is adapted to receive and deliver a liquid growth medium; (b) a fog chamber having at least a first and second inlet and a first outlet, wherein the first inlet is operably connected to the first outlet of the liquid reservoir for receiving the liquid growth medium and wherein the second inlet is operably connected to a $CO_2$ source for receiving $CO_2$, further wherein the fog chamber is adapted to produce a fog of growth medium received from the liquid reservoir; and, (c) an algal mat generator chamber having at least a first inlet operably connected to the first outlet of the fog chamber for receiving a stream of $CO_2$ and growth medium fog from the fog chamber.

Figure 1:
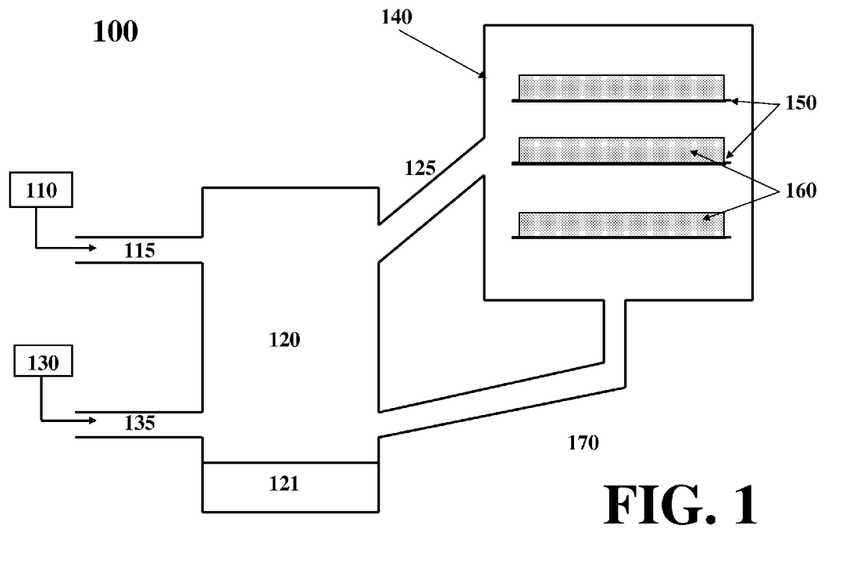
FIG. 1 is a depiction of an exemplary algae generator compatible with one or more embodiments of the present invention.

FIG. 1 illustrates one embodiment of a system 100 for generating an algae culture consistent with the present disclosure. The exemplary embodiment depicted in FIG. 1 generally comprises: a liquid reservoir 110, a fog chamber 120, an algal mat generator 130 and a light source (not depicted).

The liquid reservoir 110 is operably connected to the fog chamber 120 such that a liquid growth medium can be transported from the first outlet of the reservoir 110 to the first inlet of the fog chamber 120 through a connecting element 115. An exemplary connection is a flexible tube, although any connecting element known to one of skill in the art whereby the liquid can be pumped (not depicted) through the connecting element to a first inlet of the fog chamber 120 may be used. The fog chamber 120 may also be connected to a $CO_2$ source 130 for receiving a source of $CO_2$ in the fog chamber. The $CO_2$ may be pumped through a connecting element 135 to a second inlet of the fog chamber.

In the fog chamber 120, a liquid growth medium is nebulized into microscopic droplets and transported from a first outlet of the fog chamber through another connecting element 125 to a first inlet of the algal mat generator 140. The fog chamber 120 can be coupled to an independent nebulizing apparatus 121 or the nebulizing means can be part of the fog chamber 120. Exemplary fog chambers having a nebulizing means include but are not limited to commercial nebulizers, atomizers, jet nebulizers, ultrasonic wave nebulizers, humidifiers and vaporizers.

The algal mat generator 140 preferably comprises one or more solid support surfaces 150 that have been inoculated with an algal population 160. The algal mat generator 140 is preferably a closed environment and can be made from any material that is at least partially transparent to let sufficient light enter the generator 140. Exemplary materials included but are not limited to glass and plastic. The closed environment of the algal mat generator 140 is such that it is substantially sealed from the outside environment so that operating conditions (e.g., temperature and humidity) in the generator 140 can be maintained.

The one or more solid supports contained in the algal mat generator 140 can either be porous or non-porous, although non-porous supports are preferred because of their ease of harvesting the algae growing on them. Exemplary non-porous supports include filter paper, such as glass microfiber filters, non-woven fabrics, geotextiles, etc. Exemplary porous supports that are compatible with one or more embodiments include but are not limited to coir mats, porous fabrics, etc. A wide variety of substrates can be used with the multiple embodiments of the present invention because the substrate does not need to retain water and nutrients for algal growth as is common with most other methods because the fog produced in the fog chamber supplies the necessary water and nutrients.

In addition, the solid supports 150 can be arranged in any manner, including but not limited to vertically, horizontally and diagonally. It is preferred that the solid supports 150 be arranged in a position in which they will receive a maximum intensity of light from a light source.

Although not depicted, the $CO_2$ source 130 may be directly connected to the algal mat generator 140. While $CO_2$ may be provided from any source, it may come from industrial processes, such as flue gas emissions from coal or natural gas combustion processes, when the method and systems are used in the vicinity of such sources.

The system 100 may also include a means for recycling 170 any of the nebulized growth medium that may have condensed in the algal mat generator 140. In FIG. 1, the recycling means is depicted as a tube 170 connecting a first outlet of the generator 140 to a third inlet of the fog chamber. The condensed liquid may be returned through the tube 170 through the use of gravity or may be adapted with a pump (not depicted) that directs the flow of condensed growth medium back to the fog chamber 120.

The system 100 may also include a light source (not depicted) for providing the necessary amount of light to the algae population to facilitate algae growth. The light source may be natural sunlight or artificial light, such as UV light. Preferably, natural light is used.

In addition, the system 100 may include a means (not depicted) for collecting at least a portion of the algae cells from the solid supports. The collecting means may include but is not limited to scrapers, mechanical brushes, a belt press or similar device, or any other means known to one of skill in the art.

Figure 2:
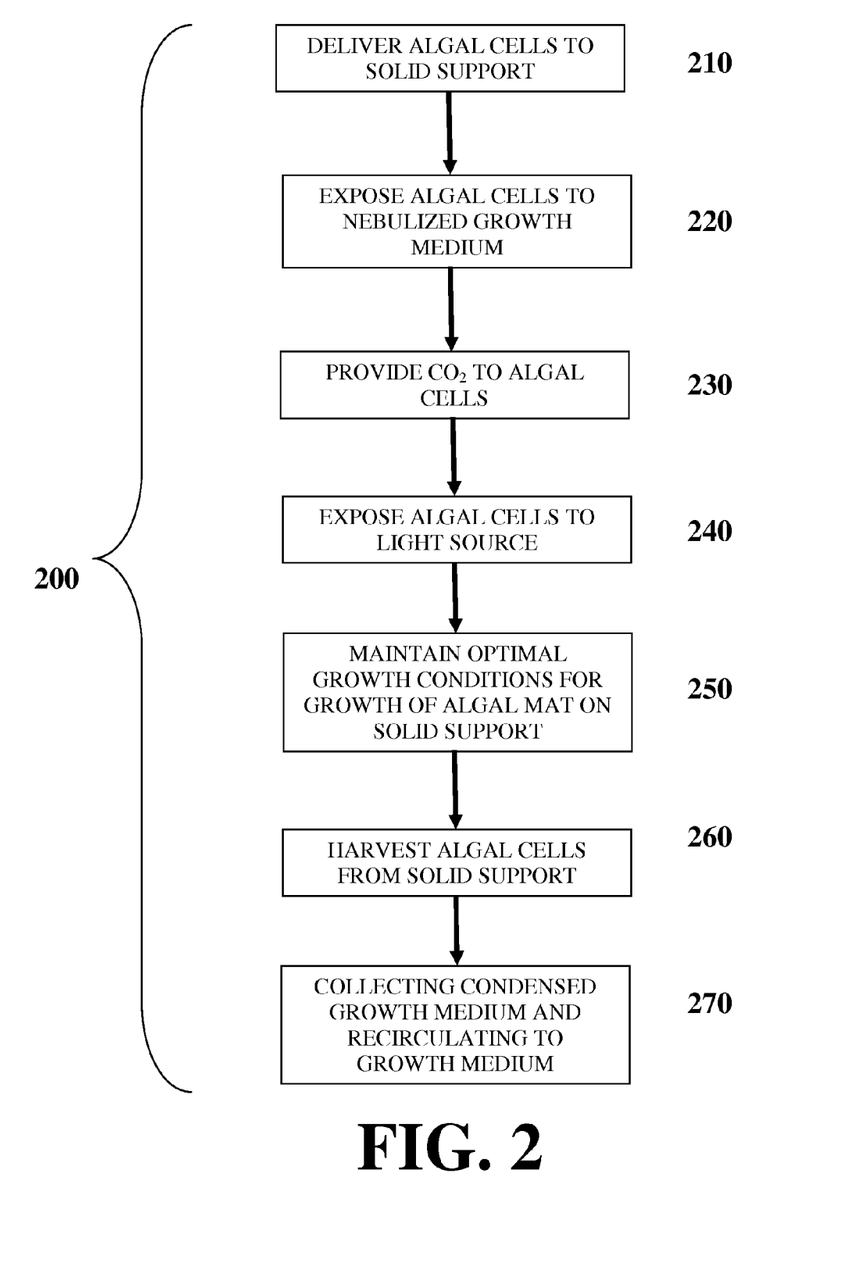
FIG. 2 is a flow diagram of one embodiment of the present invention.
Figure 3:
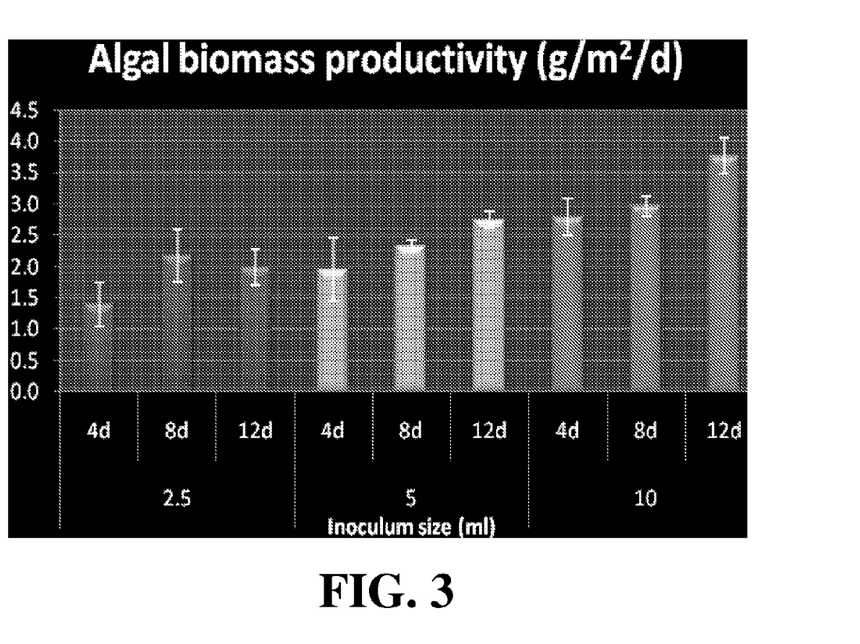
FIG. 3 is a graphical representation of the productivity ($g/m^2/d$) of mixed algal in the algal mat generator at various time intervals and inoculums levels.
Figure 4:
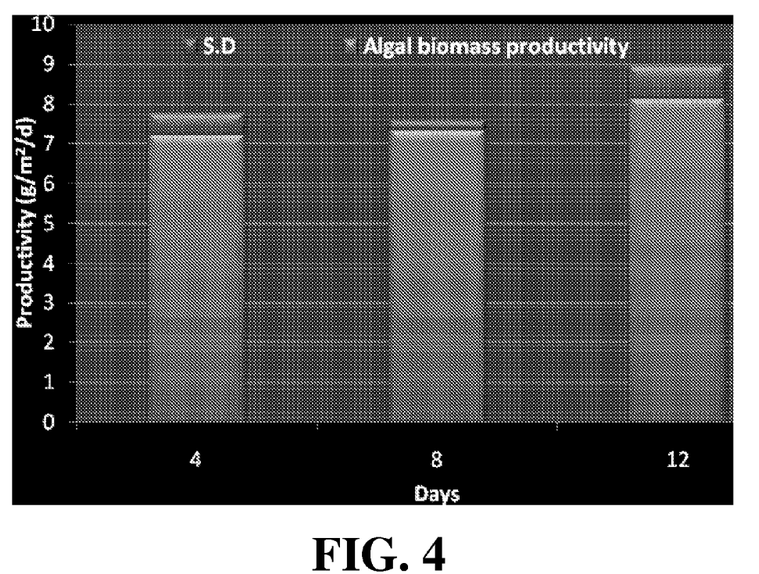
FIG. 4 is a graphical representation of biomass productivity ($g/m^2/d$) of the microalgae *C. sorokiniana* at various time intervals and a light intensity of 200 $\mu mol/m^2/s$ in a generator.

Yet another aspect of the present disclosure relates to a method 200 of culturing algae comprising: (a) delivering a population of algal cells to a solid support; (b) exposing the population of algal cells to a nebulized growth medium; and, (c) maintaining the population of algal cells under conditions suitable for growth. The method may be carried out in a system similar to that depicted in FIG. 1, but is not limited to such a system.

With reference to FIG. 2, the initial step of the method 200 comprises delivering a population of algal cells to a solid support 210. As discussed above, the solid support is preferably non-porous, but may also be porous. The population of algal cells may be delivered to the solid supports via conventional methods known to one of skill in the art, including but not limited to providing a trickling flow over the support surface at the beginning of the process, with periodic renewal, or the whole surface (if fabric in nature) may be dipped into an inoculum media at the beginning before entry into the misting chamber. This step may be performed in a closed environment where the algae cells will be cultured or may be delivered outside the closed environment and the solid supports subsequently placed in the closed environment.

In one or more embodiments of this method, the population of algal cells can comprise at least one of the group consisting of: a marine algal strain, a freshwater (non-marine) algal strain, a cyanobacter strain, a diatomaceous algal strain, a plurality of marine algal strains, a plurality of freshwater (non-marine) algal strains, a plurality of cyanobacter strains, and a plurality of diatomaceous algal strains, or any combination thereof.

In the embodiments of this aspect of the disclosure, at least one algal strain of the population of algal cells can be isolated from a source in contact with wastewater effluent of an industrial application, such as carpet industry wastewater.

In the embodiments of this aspect of the disclosure the population of algal cells can comprise an algal strain of a genus selected from the group consisting of: *Gloeocystis, Limnothrix, Scenedesmus, Chlorococcum, Chlorella, Anabaena, Chlamydomonas, Botryococcus, Cricosphaera, Spirulina, Nannochloris, Dunaliella, Phaeodactylum, Pleurochrysis, Tetraselmis*, and a combination thereof.

In the embodiments of this aspect of the disclosure, at least one algal strain of the population of algal cells can be selected from the group consisting of: a *Chlamydomonas* sp., *Chlorella vulgaris*, a *Chlorococcaceae* sp., *Chlorococcum humicola, Coelastrum microporum, Gloeocystis vesiculosa, Monoraphidium mirabile*, an *Oedogonium* sp., *Oocystis lacustris, Scenedesmus abundans, Scenedesmus acuminatus, Scenedesmus acutus, Scenedesmus acutus alternans, Scenedesmus bicaudatus, Scenedesmus bijuga, Scenedesmus bijuga alternans, Scenedesmus denticulatus, Scenedesmus dimorphus, Scenedesmus incrassatulus, Scenedesmus obliquus, Scenedesmus quadricauda, Scenedesmus quadrispina, Scenedesmus serratus*, a *Stigeoclonium* sp., *Ulothrix variabilis*, a *Uroglena* sp., an *Anabaena* sp, *Aphanocapsa delicatissima, Aphanocapsa hyalina*, an *Aphanothece* sp., *Calothrix braunii*, a *Chroococcaceae* sp., *Chroococcus minutus*, a *Cylindrospermopsis* sp., *Leibleinia kryloviana*, a *Limnothrix* sp., *Limnothrix redekei*, a *Lyngbya* sp., a *Nostoc* sp., an *Oscillatoria* sp., *Oscillatoria tenuis, Planktolyngbya limnetica, Raphidiopsis curvata, Synechococcus elongatus*, a *Synechococcus* sp., a *Synechocystis* sp., an *Eunotia* sp., *Navicula pelliculosa*, a *Navicula* sp., *Nitzschia palea, Nitzschia amphibia, Nitzschia pura, Gomphonema parvulum, Gomphonema gracile*, and a *Rhodomonas* sp.

In some embodiments of this aspect of the disclosure, the population of algal cells comprises at least one species selected from the group consisting of: *Botryococcus braunii* UTEX 572, *Chlorella protothecoides* UTEX 25, *Chlorella saccharophila* var. *saccharophila* UTEX 2469, *Chlorella vulgaris* UTEX 2714, *Cricosphaera carterae* UTEX LB1014, *Dunaliella tertiolecta* UTEX LB999, *Nannochloris oculata* UTEX LB1998, *Spirulina platensis* UTEX LB1926, *Spirulina maxima* UTEX LB2342, *Tetraselmis suecica* UTEX LB2286, *Tetraselmis chuii* UTEX LB232, *Phaeodactylum tricornutum* UTEX 646, *Pleurochrysis carterae* CCMP 647, and a combination thereof.

In some embodiments, the population of algal cells can comprise a plurality of strains selected from the Group consisting of: *Botryococcus braunii* UTEX 572, *Chlorella protothecoides* UTEX 25, *Chlorella saccharophila* var. *saccharophila* UTEX 2469, *Chlorella vulgaris* UTEX 2714, *Cricosphaera carterae* UTEX LB1014, *Dunaliella tertiolecta* UTEX LB999, *Nannochloris oculata* UTEX LB1998, *Spirulina platensis* UTEX LB1926, *Spirulina maxima* UTEX LB2342, *Tetraselmis suecica* UTEX LB2286, *Tetraselmis chuii* UTEX LB232, *Phaeodactylum tricornutum* UTEX 646, and *Pleurochrysis carterae* CCMP 647.

In an embodiment of this aspect of the disclosure, the population of algal cells can be a consortium, where the consortium comprises *Gleocytis vesiculosa* strain 1, *Limnothrix redekei, Gleocytis vesiculosa* strain 2, *Scenedesmus* spp., *Limnothrix redekei, Chlorococcum humicola* strain 1, *Chlorococcum humicola* strain 2, *Chlorococcum humicola* strain 3, *Clorella vulgaris* strain 1, *Clorella vulgaris* strain 2, *Clorella vulgaris* strain 3, *Gleocytis vesiculosa* strain 3, *Anabaena* spp., *Gleocytis vesiculosa* strain 4, *Chlamydomonas* spp. In an embodiment of this aspect of the disclosure, the population of algal cells can be a consortium comprising *Chlamydomonas globosa, Chlorella minutissima*, and *Scenedesmus bijuga*.

Following delivery of the algal cells to a solid support 210, which is preferably contained in a closed environment, the algal cells are exposed to a nebulized growth medium 220. Any liquid growth medium that supports growth of a specific algal strain or combination of strains can be used with the multiple embodiments of this method. By way of example, common growth mediums include but are not limited to CHEV diatom media, Allen medium, BG-11 medium, Bold medium, CR1 diatom medium, BG-11 medium, soilwater media, various saltwater media, industrial, agricultural or municipal wastewater, and combinations thereof, in addition to those listed in the UTEX database. Generally, it is preferred that the liquid growth medium comprise at least phosphate, nitrate, silicate and combinations thereof.

In order to create a nebulized growth medium, the liquid growth medium is subjected to conditions that produce a fine mist or fog of growth medium droplets. Various methods exist by which such droplets may be created, including but not limited to exposing the liquid to a nebulizer, an atomizer, a jet nebulizer, an ultrasonic jet nebulizer, a humidifier or a vaporizer. It is preferred that the growth medium droplet size to be delivered to the algal cells is between about 2 and 1000 microns, preferably larger than 100 microns.

Once the populations of algal cells contained on the solid supports are exposed to the nebulized growth medium, the conditions in the growth environment are to be maintained so as to maximize algal growth 250. Generally, the temperature and humidity of the growth environment are monitored and maintained. In preferred embodiments, the temperature is between about 15° C. and 35° C., and even more preferably between about 20° C. and 30° C. The humidity of the growth environment should be greater than 50%, but preferably greater than 90% and even more preferable greater than 99%. Additionally, the closed environment can be equipped with other sensing systems that can monitor other environmental conditions, such as oxygen and carbon dioxide levels.

Optionally, and preferably, one or more embodiments include an additional step of exposing the population of algal cells to a light source 240, which can be either natural or artificial. Preferably, the light source is natural sunlight. In alternative embodiments, the light source may be artificial, such as fluorescent tube lights. Further, it is preferred that the populations of algal cells on the solid supports and the light source(s) are positioned such that a maximum intensity of light reaches the algal cells. In certain embodiments, the intensity of light is between about 100 and 200 $\mu mol/m^2/s$, but a wide range of light intensity will promote algal growth. For example, light intensity greater than 200 $\mu mol/m^2/s$ may be necessary if the misting environment of the growth chamber causes sufficient light dispersion.

Optionally, and also preferably, a source of $CO_2$ 230 can be provided to the population of algal cells in the growth environment. The concentration of $CO_2$ provided to the algal cells can be a broad range depending on other operating conditions, and can be between about 5-10% in the case of a typical flue gas $CO_2$ source. However, any concentration of $CO_2$ coming from a coal or natural gas combustion process will likely be compatible with the multiple embodiments. The $CO_2$ can be introduced to the algal cells in the growth environment directly from a $CO_2$ source or may be pumped through a chamber in which the liquid growth medium is nebulized in order to carry the nebulized growth medium to the growth environment.

Further, in order to use the algal cells for the intended use, it will be necessary to collect and isolate 260 the algal cells from the solid supports. Various methods exist in which to accomplish this objective, including but not limited to scrapers.

Further, as the nebulized liquid growth medium is introduced to the closed environment containing the algal cells, it is likely that a portion of the liquid medium will condense on the surfaces inside the closed environment. In order to maximize use of the liquid growth medium, the method may also include a step of collecting and recirculating 270 the liquid growth medium to the fog chamber for reuse. Various methods can be used to collect and return the condensed liquid growth medium, including allowing the medium to naturally flow into a connecting tube where it can be pumped back to the liquid growth medium source.

The specific examples below are to be construed as merely illustrative, and not limiting of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide one of ordinary skill in the art with a complete disclosure and description of how to perform the methods and systems disclosed herein.

It should be noted that ratios, concentrations, amounts, and other numerical data may be expressed herein in a range format or as an approximation. It is to be understood that such a range or approximation is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include .+–0.1%, .+–0.2%, .+–0.3%, .+–0.4%, .+–0.5%, .+–0.6%, .+–0.7%, .+–0.8%, .+–0.9%, or .+–0.10%, or more of the numerical value(s) being modified.

Example 1

In these examples, a modified version of a 10 gallon aquarium tank with an acrylic lid to create a closed environment was used as the fog algal mat generator. The generator included a platform that held the solid supports out of the water. A fog chamber was connected to the generator with ½ inch diameter tubing. The fog was created using a nebulizer that was operably connected to the fog chamber. The nebulizer created a fog with droplet sizes between about 2-10 microns and was delivered to the generator through the tubing by pumping a 5-10% $CO_2$ mixture at a flow rate of 3 L/minute through the fog chamber.

Predried and preweighed Whatman GF/C glass microfiber filters (48 mm diameter) were used as the solid support and to establish a biofilm and quantify biomass production. A control group consisted of GF/C filters washed with 10 mL of deionized water. A second group of filter papers were inoculated with 2.5 mL of mixed algal culture inoculum derived from a wastewater. A third and fourth group of filter papers were inoculated with 5 mL and 10 mL of mixed algal culture, respectively. Inoculation of the second, third and fourth groups of filter paper was accomplished by filtering the mixed algal culture through the filter paper, followed by rinsing with 10 mL deionized water and 15 seconds of suction. Estimated initial weight of algal inoculum was obtained by drying three samples from each group in a forced-air oven at 60° C. for 24 hours. The remaining samples were placed on the platform in the generator.

Light intensity within the generator during active fogging was maintained at 100 $\mu mol/m^2/s$. The conditions were maintained for 12 days under 12/12 hour light/dark cycles at 25° C. BG 11 growth medium was nebulized to create the nutrient fog and about 10 liters of growth medium were nebulized during the 12 days period, although a significant amount of condensation occurred on the inside walls of the generator and collected at the bottom.

Samples were collected, rinsed with 10 mL deionized water and dried in the forced-air oven at 60° C. for 24 hours at 4, 8 and 12 days. These samples were weighed, averaged and compared against the day 0 (initial inoculum) samples from the same treatment. The difference in the mass of the two was the total productivity for the samples on that day and productivity/$m^2$/day was estimated as described in Table #.

TABLE 1

| Inoculum | Inoculum Size/Weight (mL/g) | Light Intensity ($\mu mol/m^2/s$) | Productivity ($g/m^2/day$) | | |
|---|---|---|---|---|---|
| | | | 4 day | 8 day | 12 day |
| Mixed Algal | 2.5 | 100 | 1.4 | 2.2 | 2 |
| Mixed Algal | 5 | 100 | 1.9 | 2.3 | 2.8 |
| Mixed Algal | 10 | 100 | 2.8 | 3.0 | 3.8 |

Example 2

In another example, 2.5 mL of *Chlorella sorokiniana* (a green algae) was inoculated as describes in Example 1 to assess its production ability. However, the light intensity was increased to 200 $\mu mol/m^2/s$ and the experiment was conducted for 12 days under continuous illumination. Biomass productivity was found to be 8.2 $g/m^2/day$ with the increased light intensity.

TABLE 2

| Inoculum | Inoculum Size/Weight (mL/g) | Light Intensity ($\mu mol/m^2/s$) | Productivity ($g/m^2/day$) 12 day |
|---|---|---|---|
| *C. sorokiniana* | 2.5 | 200 | 8.2 |

Based on the foregoing results, it is apparent that one or more embodiments of the present invention present a viable method and system for culturing algae. Further, it is possible, and beneficial, to include multiple layers of supports in the generator that can be arranged vertically, horizontally, diagonally or any other angle that would improve biomass productivity with proper lighting arrangements. For example, using the results from Example 2, if ten support surfaces were included in the generator, the theoretical production in a generator having a 1 m² footprint would be approximately 82 g/m²/d, which is far greater than productivity of most current photobioreactors and raceway ponds.

It is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

We claim:

1. A system for culturing algae comprising:
   (a) a liquid reservoir having at least a first inlet and a first outlet, wherein the liquid reservoir is adapted to receive and deliver a liquid growth medium;
   (b) a fog chamber having at least a first and second inlet and a first outlet, wherein the first inlet is operably connected to the first outlet of the liquid reservoir for receiving the liquid growth medium and wherein the second inlet is operably connected to a $CO_2$ source for receiving $CO_2$, further wherein the fog chamber is adapted to produce a fog of growth medium received from the liquid reservoir;
   (c) an enclosed algal mat generator chamber having at least a first inlet operably connected to the first outlet of the fog chamber for receiving a stream of $CO_2$ and growth medium fog from the fog chamber; and,
   (d) a light source, wherein the illumination source is disposed such that it provides a maximum intensity of light to the algal mat generator chamber to support growth of algae in the algal mat generator chamber.

2. The system of claim 1, further comprising at least one solid support surface within the algal mat generator chamber, wherein the solid support surface is compatible for formation of an algal mat thereon.

3. The system of claim 1, further comprising a plurality of solid support surfaces in the algal mat generator that are compatible for the formation of a plurality of algal mats thereon.

4. The system of claim 3, wherein the solid support surfaces are arranged vertically.

5. The system of claim 3, wherein the solid support surfaces are arranged horizontally.

6. The system of claim 2, wherein the solid support surface is non-porous.

7. The system of claim 2, wherein the algal mat generator chamber further comprises at least a first outlet and the fog chamber further comprises a third inlet, wherein the first outlet of the algal mat generator is operably connected to the third inlet of the fog chamber for the recirculation of condensed growth medium to the fog chamber.

8. The system of claim 2, further comprising means for removing at least a portion of the algal mat from the solid support surface.

9. The system of claim 2, wherein the fog chamber is selected from the group consisting of: a nebulizer, a jet nebulizer, an ultrasonic wave nebulizer, humidifier and vaporizer.

10. The system of claim 2, wherein the light source is artificial.

11. The system of claim 2, wherein the system includes a means for collecting a portion of algal cells from said solid support.

* * * * *